United States Patent [19]
Guillemette et al.

[11] 4,425,274
[45] Jan. 10, 1984

[54] NOVEL PROCESS FOR THE PRODUCTION OF URSODESOXYCHOLIC ACID

[75] Inventors: Armand Guillemette, Noisy-le-Sec; Abel François, Bondy, both of France

[73] Assignee: Roussel UCLAF, Paris, France

[21] Appl. No.: 398,422

[22] Filed: Jul. 14, 1982

Related U.S. Application Data

[63] Continuation of Ser. No. 98,764, Nov. 30, 1979, abandoned.

[30] Foreign Application Priority Data

Dec. 15, 1978 [FR] France .................... 78 35358

[51] Int. Cl.³ .................................................. C07J 9/00
[52] U.S. Cl. .................................................. 260/397.1
[58] Field of Search ...................................... 260/397.1

[56] References Cited

U.S. PATENT DOCUMENTS 4,282,161  8/1981  Guillemette .................... 260/397.1

OTHER PUBLICATIONS

Kiek, "Steroid Reaction Mechanisms", (1968) Elsevier Publishing Co., (New York), pp. 131-143.
Anderson et al., "Journal of Biochemistry", (1962), pp. 236-242.
Djerassi et al., "Steroid Reactions", (1963), Holden--Day Inc. pp. 276-277.

Primary Examiner—Elbert L. Roberts
Attorney, Agent, or Firm—Hammond & Littell, Weissenberger and Muserlian

[57] ABSTRACT

An improved process for the preparation of ursodesoxycholic acid or 3α,7β-dihydroxy-cholanic acid in high yields by reducing 3α-hydroxy-7-keto-cholanic acid with lithium in liquid ammonia.

6 Claims, No Drawings

PROCESS FOR THE PRODUCTION OF URSODESOXYCHOLIC ACID

PRIOR APPLICATION

This application is a continuation of our copending, commonly assigned U.S. patent application Ser. No. 98,764 filed Nov. 30, 1979 now abandoned.

STATE OF THE ART

It is known to produce ursodesoxycholic acid by a series of reactions beginning from chenodesoxycholic acid as described by Kamazawa et al [Chem. Ab., Vol. 51 (1957), p. 17965] and the last step consists of reducing $3\alpha$-hydroxy-7-keto-cholanic acid with sodium in isopropanol to obtain ursodesoxycholic acid. Japanese patent application Ser. No. 154,865 of 1975 describes the reduction of $3\alpha$-hydroxy-7-keto-cholanic acid with sodium in the presence of tertbutanol and Japanese patent application Ser. No. 82,722 of 1975 also describes the reduction of $3\alpha$-hydroxy-7-keto-cholanic acid with potassium in the presence of tert.-butanol.

However, the use of potassium requires a very high degree of caution and presents serious disadvantages for industrial use. Moreover, reduction of $7\alpha$-hydroxy-7-keto-cholanic acid with sodium or potassium results in substantial formation of $3\alpha,7\alpha$-dihydroxy-cholanic acid (chenodesoxycholic acid) as well as the desired $3\alpha,7\beta$-dihydroxy-cholanic acid. Other prior art includes French Pat. Nos. 1,372,109 and 1,391,735.

OBJECTS OF THE INVENTION

It is an object of the invention to provide an improved process for the reduction of $3\alpha$-hydroxy-7-keto-cholanic acid with yields of the order of 90% of $3\alpha,7\beta$-dihydroxy-cholanic acid.

These and other objects and advantages of the invention will become obvious from the following detailed description.

THE INVENTION

The novel process of the invention for the preparation of $3\alpha,7\beta$-dihydroxy-cholanic acid comprises reducing $3\alpha$-hydroxy-7-keto-cholanic acid with lithium in liquid ammonia in the presence of a proton donor to form lithium $3\alpha,7\beta$-dihydroxy-cholanate and reacting the latter with an acid to form $3\alpha,7\beta$-dihydroxy-cholanic acid.

The process of the invention results in yields of the desired $3\alpha,7\beta$-dihydroxy-cholanic acid on the order of 90% containing only about 10% of $3\alpha,7\beta$-dihydroxy-cholanic acid.

The proton donor may be an alkanol or an ammonium salt. Examples of suitable alkanols are alkanols of 1 to 4 carbon atoms such as methanol, ethanol, propanol and tert.-butanol and examples of suitable ammonium salts are ammonium chloride and ammonium acetate. The preferred proton donor is methanol.

The reduction step is preferably effected in an organic solvent of the ether-oxide type such as tetrahydrofuran. The reaction is preferably effected at $-70°$ C. to the boiling point of ammonia, most preferably the latter. The reaction of the lithium salt with an acid is preferably effectd with an inorganic acid such as sulfuric acid or hydrochloric acid, most preferably the latter.

In the following example there are described several preferred embodiments to illustrate the invention. However, it is to be understood that the invention is not intended to be limited to the specific embodiments.

EXAMPLE

A mixture of 100 g of $3\alpha$-hydroxy-7-keto-cholanic acid, 1000 ml of tetrahydrofuran and 30 ml of methanol was stirred until dissolution occured and the solution was cooled to $-32°$ C. Then, 1000 ml of liquid ammonia were added thereto all at once and then 10 g of lithium in small particles were added thereto at $-32°$ C. over 45 to 60 minutes. 100 ml of methanol were added to the mixture over 15 minutes and the ammonia was evaporated by placing the mixture in a water bath at 30° C. for one hour. 400 ml of demineralized water were added all at once to the reaction mixture which was then adjusted to a pH of $\simeq 2$ by addition of 200 ml of 22° Bè hydrochloric acid. The mixture was extracted four times with 200 ml of ethyl acetate and the organic phase was washed with demineralized water and evaporated to dryness of 60° C. under reduced pressure. The residue was taken up 3 times with 100 ml of ethyl acetate and the organic phase was evaporated to dryness at 70° C. under reduced pressure to obtain 104 g of crystalline crude $3\alpha,7\beta$-dihydroxy-cholanic acid with a specific rotation of $[\alpha]_D^{20} = +50° \pm 1°$ (c=1% in ethanol). Thin layer chromatograpy showed the raw product contained about 8% of chenodesoxycholic acid ($3\alpha,7\alpha$-dihydroxy-$5\beta$-cholanic acid).

Various modifications of the process of the invention may be made without departing from the spirit or scope thereof and it should be understood that the invention is intended to be limited only as defined in the appended claims.

What is claimed is:

1. A process for the preparation of $3\alpha,7\beta$-dihydroxy-cholanic acid comprising reducing $3\alpha$-hydroxy-7-keto-cholanic acid with lithium in liquid ammonia in the presence of a proton donor to form lithium $3\alpha,7\beta$-dihydroxy-cholanate and reacting the latter with an acid to form $3\alpha,7\beta$-dihydroxy-cholanic acid.

2. The process of claim 1 wherein the proton donor is an alkanol.

3. The process of claim 1 wherein the proton donor is methanol.

4. The process of claim 1 wherein the reaction is effected in an ether-oxide solvent.

5. The process of claim 4 wherein the solvent is tetrahydofuran.

6. The process of claim 1 wherein the acid is hydrochloric acid.

* * * * *